United States Patent [19]

Tegeler et al.

[11] Patent Number: 4,562,187

[45] Date of Patent: Dec. 31, 1985

[54] (ISOXAZOL-3-YL)ARYLMETHANONES, COMPOSITIONS AND PHARMACEUTICAL USE

[75] Inventors: John J. Tegeler, Bridgewater; Craig J. Diamond, North Wales, Pa.

[73] Assignee: Hoechst-Roussel Pharmaceuticals Inc., Somerville, N.J.

[21] Appl. No.: 693,508

[22] Filed: Jan. 22, 1985

[51] Int. Cl.[4] .................. A61K 31/42; A61K 31/535; C07D 261/06; C07D 413/06
[52] U.S. Cl. .................................... 514/238; 544/137; 544/367; 548/248; 514/240; 514/255; 514/378
[58] Field of Search ................ 544/137, 367; 548/248; 514/238, 240, 255, 378

[56] References Cited

U.S. PATENT DOCUMENTS 4,247,548  1/1981  Yoshimoto et al. .................. 544/21

FOREIGN PATENT DOCUMENTS 2166467  2/1974  Fed. Rep. of Germany .
2422667  11/1979  France .
5821616  2/1983  Japan .

OTHER PUBLICATIONS

Sasaki et al., *Bull. Chem. Soc. Japan*, vol. 44, (1971), pp. 185–189.

Primary Examiner—Robert W. Ramsuer
Attorney, Agent, or Firm—Tatsuya Ikeda

[57] ABSTRACT

There are disclosed novel compounds having the formula

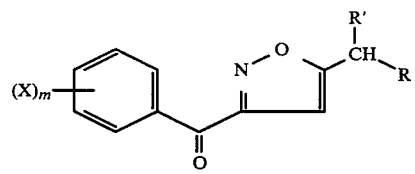

where each X is independently hydrogen, halogen (F, Cl, Br or I), loweralkyl or loweralkoxy; m is 1 or 2; R' is hydrogen or loweralkyl; and R is

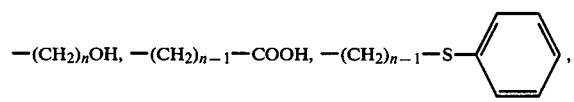

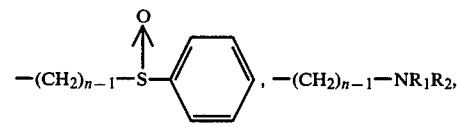

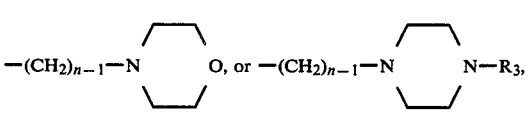

n being 1, 2 or 3, each of $R_1$ and $R_2$ being independently hydrogen or loweralkyl and $R_3$ being

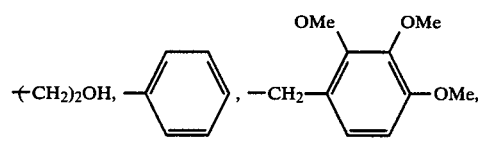

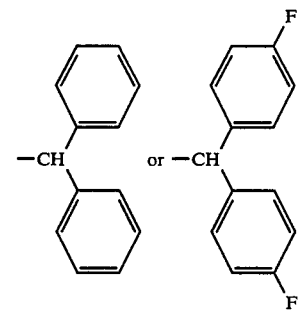

an optical antipode thereof or a pharmaceutically acceptable acid addition salt thereof, which are useful as antihypertensive, analgesic and antiinflammatory agents, methods for synthesizing them, and pharmaceutical compositions comprising an effective amount of such a compound.

118 Claims, No Drawings

(ISOXAZOL-3-YL)ARYLMETHANONES, COMPOSITIONS AND PHARMACEUTICAL USE

This invention relates to novel compounds of the formula

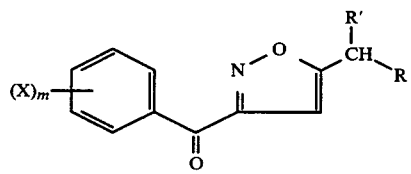

where each X is independently hydrogen, halogen (F, Cl, Br or I), loweralkyl or loweralkoxy; m is 1 or 2; R' is hydrogen or loweralkyl; and R is

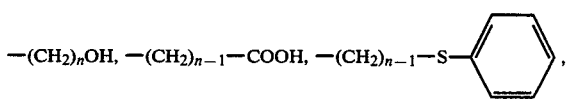

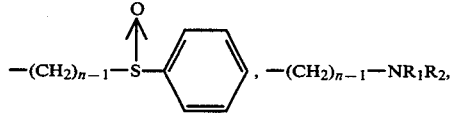

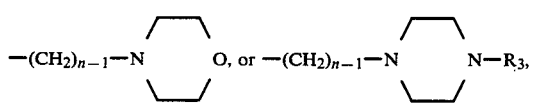

n being 1, 2 or 3, each of $R_1$ and $R_2$ being independently hydrogen or loweralkyl and $R_3$ being

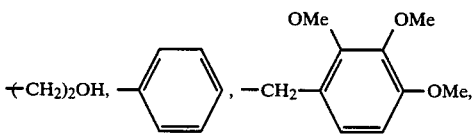

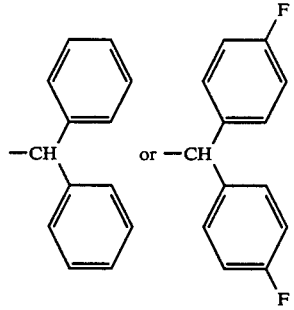

an optical antipode thereof or a pharmaceutically acceptable acid addition salt thereof, which are useful as antihypertensive, analgesic and antiinflammatory agents, methods for synthesizing them, and pharmaceutical compositions comprising an effective amount of such a compound.

Unless otherwise stated or indicated, the term loweralkyl donates a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched chain pentoxy and hexoxy.

Unless otherwise stated or indicated, the term halogen shall mean fluorine, chlorine, bromine or iodine.

The compounds of the present invention are prepared by following one or more of the steps described below. Throughout the description of the synthetic steps, the definitions of X, m, R', R, $R_1$, $R_2$, $R_3$ and n are as given above unless otherwise stated or indicated.

STEP A

A compound of Formula IV below is prepared by a cyclo-addition reaction between a compound of Formula II and an alcohol of Formula III.

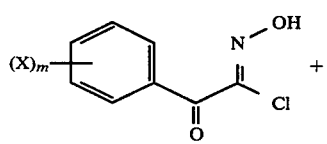

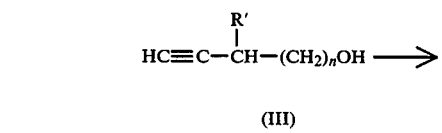

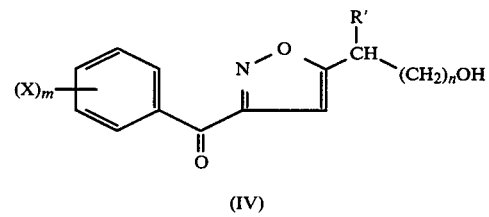

Typically, said cyclo-addition reaction is conducted at a temperature of 100°–150° C. in a suitable medium such as an excess of said alcohol of Formula III.

STEP B

A compound of Formula V below is prepared by oxidizing compound IV with a suitable oxidizing agent including hexavalent chromium compounds such as $K_2Cr_2O_7$, $Na_2Cr_2O_7$ and $CrO_3$, and heptavalent manganese compounds such as $KMnO_4$.

IV ⟶

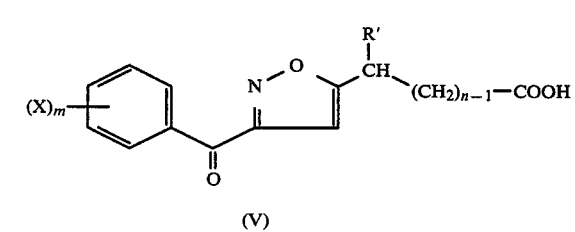

Typically, said oxidation reaction is conducted in the presence of pulverized $K_2Cr_2O_7$, concentrated sulfuric acid and a catalytic amount of $Bu_4NHSO_4$ in a suitable solvent such as dichloromethane, chloroform or the like at a temperature of about 0°–50° C.

STEP C

A compound of Formula VI is prepared by the cyclo-addition reaction between compound II and a compound of Formula VII.

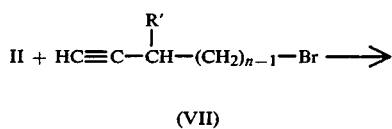

Typically, said cyclo-addition reaction is conducted in a suitable solvent including aromatic hydrocarbons such as toluene, benzene, xylene or the like at a temperature of about 80°–130° C.

STEP D

A compound of Formula VIII below is prepared by reacting compound VI with phenyl mercaptan.

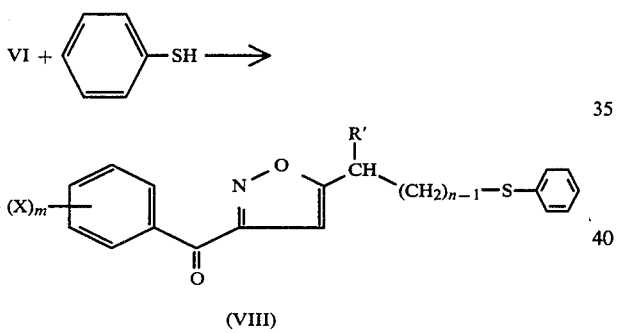

Said reaction is usually conducted in the presence of a base such as triethylamine, pyridine, sodium hydride or the like in a suitable solvent including acetone, ethereal compounds such as diethyl ether, tetrahydrofuran, dioxane or the like, and dimethylformamide at a temperature of about 20°–60° C.

STEP E

A compound of Formula IX below is prepared by oxidizing compound VII with a suitable peroxy compound such as, for instance, m-chloroperoxybenzoic acid.

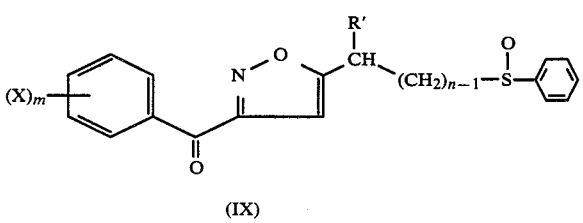

Typically, said oxidation reaction is conducted in a suitable solvent such as dichloromethane at a low temperature of from about −80° C. to about −60° C.

STEP F

A compound of Formula X below is prepared by reacting compound VI with an amine of the formula $HNR_1R_2$.

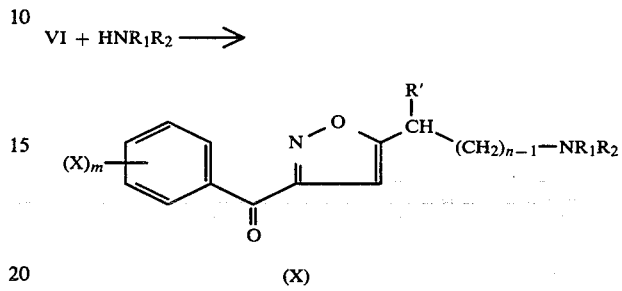

Typically, when said amine is a gas as in the case of dimethylamine, the amine gas is bubbled into a suitable solvent including alcohols such as methanol, ethanol and propanol, ethereal compounds such as diethyl ether, tetrahydrofuran and dioxane and mixtures thereof, in order to saturate the solvent with the amine and then the resultant saturated solution is added to a solution of compound VI in a suitable solvent such as those mentioned above. When said amine is a liquid, the reaction mixture is prepared simply by dissolving the two reactants in a suitable solvent such as those mentioned above. The reaction is usually conducted at a temperature of about 20°–100° C.

STEP G

A compound of Formula XI below is prepared by reacting compound VI with morpholine.

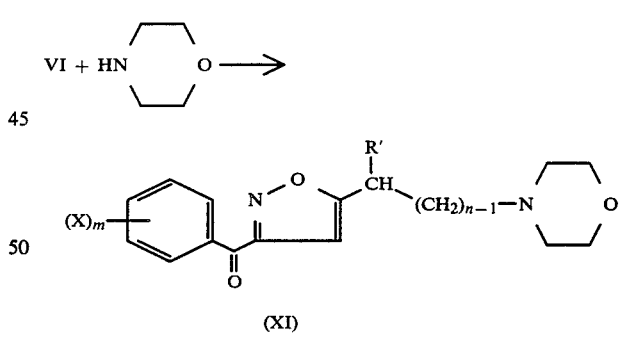

Said reaction is conducted in substantially the same manner as described in STEP F.

STEP H

A compound of Formula XII below is prepared by reacting compound VI with a compound of Formula XIII.

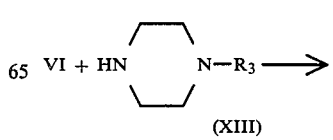

-continued

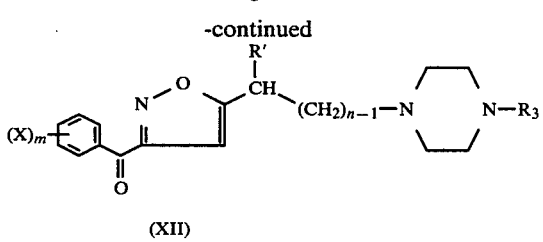

(XII)

Said reaction is conducted in substantially the same manner as described in STEP F.

In conducting the reactions described in STEPS F, G and H above, it is often convenient or advantageous to add a tertiary amine such as triethylamine and an inorganic base such as potassium carbonate or the like to the reaction medium.

The compounds of the present invention are useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals are treated orally for three days with the test compound in relation to a control group of the same number. The drop in blood pressure is measured on the third day following administration. The antihypertensive activities of some of the compounds, expressed as a decrease in mean arterial blood pressure (in mm Hg), are given in Table I along with the activity of a standard compound.

The compounds of the present invention are also useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Table I shows a result of the test of the analgesic activities of some of the compounds of this invention along with the activity of a standard compound.

The compounds of the present invention are also useful as antiinflammatory agents due to their ability to suppress inflammation in mammals. The activity of the compounds is demonstrated in the carrageenin induced rat paw edema antiinflammatory assay [Proc. Soc. Exptl. Biol. Med., III 544 (1962), J. Pharmacol. Exp., 141 (1963)]. The results of the antiinflammatory test of some of the compounds of this invention are given in Table I along with a result for a standard compound.

TABLE I

|  | SHR mm dec. in BP @ 50 mg/kg p.o. | CPE % dec. @ 100 mg/kg p.o. | PQW % dec. |
| --- | --- | --- | --- |
| 4-Chlorophenyl-[(5-phenylsulfinyl-methyl)-isoxazol-3-yl]methanone | — | — | 19 @ 25 mg/kg p.o. |
| 4-Chlorophenyl-[(5-phenylthio-methyl)-isoxazol-3-yl]methanone | — | — | 27 @ 25 mg/kg p.o. |
| (5-(Morpholin-4-yl)-methylisoxazol-3-yl]-4-fluorophenylmethanone | — | — | $ED_{50}$ = 11.5 s.c. |
| [5-(4-Benzhydryl-piperazin-1-yl)methyl-isoxazol-3-yl]-phenyl-methanone dimaleate | 65 | — | — |
| [5-(4-Benzhydryl-piperazin-1-yl)methyl-3-yl]-4-chlorophenyl-methanone dimaleate | — | — | 90 @ 20 mg/kg s.c. |
| [5-(4-Benzhydryl-piperazin-1-yl)methyl-isoxazol-3-yl]-4-fluoro-phenylmethanone dimaleate | 60 | 23 | — |
| [5-(4-Benzhydryl-piperazin-1-yl)methyl-isoxazol-3-yl]-4-methoxyphenylmethanone dimaleate | — | 30 | — |
| [5-[4-(4,4'-Difluoro-benzhydryl)-piperazin-1-yl]-methylisoxazol-3-yl]-4-methoxyphenyl-methanone dimaleate | 23 | — | 48 @ 20 mg/kg s.c. |
| 2-[3-(4-Toluoyl)-isoxazol-5-yl]-ethanol | — | — | 37 @ 25 mg/kg p.o. |
| 2-(3-Benzoylisoxazol-5-yl)-ethanol | — | — | 54 @ 25 mg/kg p.o. |
| 4-[3-(4-Chlorobenzoyl)-isoxazol-5-yl]butan-1-ol | — | 34 | 55 @ 25 mg/kg p.o. |
| 2-[3-(2,4-Dichloro-benzoyl)-isoxazol-5-yl]ethanol | — | 29 | 59 @ 25 mg/kg p.o. |
| 2-[3-(4-Chlorobenzoyl)-isoxazol-5-yl]propionic | — | — | 66 @ 25 mg/kg p.o. |

TABLE I-continued

| | SHR mm dec. in BP @ 50 mg/kg p.o. | CPE % dec. @ 100 mg/kg p.o. | PQW % dec. |
|---|---|---|---|
| acid | | | |
| [3-(2,4-Dichloro-benzoyl)-isoxazol-5-yl]acetic acid | — | — | 47 @ 25 mg/kg p.o. |
| [3-(4-Methoxybenzoyl)-isoxozol-5-yl]acetic acid | — | 48 | 43 @ 25 mg/kg p.o. |
| (prior art compounds) | | | |
| Methyldopa | 40 | — | — |
| Aspirin | | $ED_{50}$ = 130 mg/kg, p.o. | |
| Propoxyphene | | | $ED_{50}$ = 24.6 mg/kg, p.o. |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conventiently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxidel; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
2-(3-Benzoylisoxazol-5-yl)ethanol;
2-[3-(4-Fluorobenzoyl)isoxazol-5-yl]ethanol;
2-[3-(4-Chlorobenzoyl)isoxazol-5-yl]ethanol;
2-[3-(4-Toluoyl)isoxazol-5-yl]ethanol;
2-[3-(4-Methoxybenzoyl)isoxazol-5-yl]ethanol;
2-[3-(2,4-Dichlorobenzoyl)isoxazol-5-yl]ethanol;
2-[3-(4-Chlorobenzoyl)isoxazol-5-yl]propan-1-ol;
4-(3-Benzoylisoxazol-5-yl)butan-1-ol;
4-[3-(4-Chlorobenzoyl)isoxazol-5-yl]butan-1-ol;
4-[3-(4-Toluoyl)isoxazol-5-yL]butan-1-ol;
4-[3-(2,4-Dichlorobenzoyl)isoxazol-5-yL]butan-1-ol;
(3-Benzoylisoxazol-5-yl)acetic acid;
[3-(4-Fluorobenzoyl)isoxazol-5-yl]acetic acid;
[3-(4-Chlorobenzoyl)isoxazol-5-yl]acetic acid;
[3-(4-Toluoyl)isoxazol-5-yl]acetic acid;
[3-(4-Methoxybenzoyl)isoxazol-5-yl]acetic acid;
[3-(2,4-Dichlorobenzoyl)isoxazol-5-yl]acetic acid;
2-[3-(4-Chlorobenzoyl)isoxazol-5-yl]propionic acid;
4-Chlorophenyl-[(5-phenylthiomethyl)isoxazol-3-yl]methanone;

4-Chlorophenyl-[(5-phenylsulfinylmethyl)isoxazol-3-yl]methanone;
(5-Dimethylaminomethylisoxazol-3-yl)-4-fluorophenylmethanone;
(5-(Morpholin-4-yl)methylisoxazol-3-yl]-4-fluorophenylmethanone;
[5-(Morpholin-4-yl)methylisoxazol-3-yl]-4-chlorophenylmethanone;
[5-(4-beta-Hydroxyethylpiperazin-1-yl)methylisoxazol-3-yl]-4-fluorophenylmethanone;
[5-[(4-Phenylpiperazin-1-yl)methyl]isoxazol-3-yl]phenylmethanone;
[5-(4-Phenylpiperazin-1-yl)methylisoxazol-3-yl]-4-fluorophenylmethanone;
[5-[4-(2,3,4-Trimethoxybenzyl)piperazin-1-yl]methylisoxazol-3-yl]-4-fluorophenylmethanone;
[5-[4-(2,3,4-Trimethoxybenzyl)piperazin-1-yl]methylisoxazol-3-yl]-4-methoxyphenylmethanone;
[5-(4-Benzhydrylpiperazin-1-yl)methylisoxazol-3-yl]phenylmethanone;
[5-(4-Benzhydrylpiperazin-1-yl)methylisoxazol-3-yl]-4-fluorophenylmethanone;
[5-(4-Benzhydrylpiperazin-1-yl)methylisoxazol-3-yl]-4-chlorophenylmethanone;
[5-(4-Benzhydrylpiperazin-1-yl)methylisoxazol-3-yl]-4-methoxyphenylmethanone;
[5-[4-(4,4'-Difluorobenzhydryl)piperazin-1-yl]methylisoxazol-3-yl]-phenylmethanone;
[5-[4-(4,4'-Difluorobenzhydryl)piperazin-1-yl]methylisoxazol-3-yl]-4-fluorophenylmethanone;
[5-[4-(4,4'-Difluorobenzhydryl)piperazin-1-yl]methylisoxazol-3-yl]-4-chlorophenylmethanone; and
[5-[4-(4,4'-Difluorobenzhydryl)piperazin-1-yl]methylisoxazol-3-yl]-4-methoxyphenylmethanone.

The following examples are given for illustrative purposes and are not to be considered as limiting the invention disclosed herein. All temperatures are given in degrees Celcius.

EXAMPLE 1

2-(3-Benzoylisoxazol-5-yl)ethanol

A solution of 12 g of phenylglyoxylohydroxamyl chloride in 30 ml of 3-butyn-1-ol was refluxed under $N_2$ for 3 hours. Concentration of the product gave an oil which was purified by high pressure liquid chromatography with 5% ethyl acetate/$CH_2Cl_2$ used as an eluent to give 9.6 g (67%) of an oil.

ANALYSIS: Calculated for $C_{12}H_{11}NO_3$: 66.35%C; 5.11%H; 6.45%N; Found: 66.49%C; 5.22%H; 6.29%N.

EXAMPLE 2

2-[3-(4-Fluorobenzoyl)isoxazol-5-yl]ethanol

A solution of 12.1 g of 4-fluorophenylglyoxylohydroxamyl chloride in 30 ml of 3-butyn-1-ol was refluxed under $N_2$ for 2.5 hours. Concentration of the product on a rotovapor under high-vacuum gave 17 g of an oil. The residue was purified by high pressure liquid chromatography with 5% ethyl acetate/$CH_2Cl_2$ to yield 5.2 g (37%) of an oil which solidified on standing, m.p. 42°–45°.

ANALYSIS: Calculated for $C_{12}H_{10}FNO_3$: 61.27%C; 4.29%H; 5.95%N; Found: 61.30%C; 4.47%H; 5.84%N.

EXAMPLE 3

2-[3-(4-Chlorobenzoyl)isoxazol-5-yl]ethanol

A solution of 12 g of 4-chlorophenylglyoxylohydroxamyl chloride in 30 g of 3-butyn-1-ol was refluxed under $N_2$ for 2.5 hours. Concentration of the product on a rotovapor under high vacuum gave 17 g of an oil. Purification by high pressure liquid chromatography with 5% ethyl acetate/$CH_2Cl_2$ yielded 11.8 g (85%) of an oil which solidified on standing, m.p. 59°–62°.

ANALYSIS: Calculated for $C_{12}H_{10}ClNO_3$: 57.27%C; 4.01%H; 5.57%N; Found: 57.66%C; 4.18%H; 5.39%N.

EXAMPLE 4

2-[3-(4-Toluoyl)isoxazol-5-yl]ethanol

A solution of 10 g of 4-tolylglyoxylohydroxamyl chloride in 35 ml of 3-butyn-1-ol was refluxed under $N_2$ for 6 hours. Concentration of the product gave an oil which was purified by high pressure liquid chromatography with 7% ethyl acetate/$CH_2Cl_2$ used as an eluent to give 7.7 g (67%) of an oil.

ANALYSIS: Calculated for $C_{13}N_{13}NO_3$: 67.52%C; 5.67%H; 6.06%N; Found: 67.30%; 5.69%H; 5.69%N.

EXAMPLE 5

2-[3-(4-Methoxybenzoyl)isoxazol-5-yl]ethanol

A solution of 17.0 g of 4-methoxyphenylglyoxylohydroxamyl chloride in 40 ml of 3-butyn-1-ol was refluxed under $N_2$ for 4 hours. Concentration of the product on a rotovapor under a high vacuum gave 25 g of an oil. The residue was purified by high pressure liquid chromatography with 15% ethyl acetate/$CH_2Cl_2$ to yield 14.1 g (71%) of an oil.

ANALYSIS: Calculated for $C_{13}H_{13}NO_4$: 63.14%C; 5.31%H; 5.66%N; Found: 62.71%C; 5.45%H; 5.56%N.

EXAMPLE 6

2-[3-(2,4-Dichlorobenzoyl)isoxazol-5-yl]ethanol

A solution of 25.2 g of 2,4-dichlorophenylglyoxylohydroxamyl chloride in 50 ml of 3-butyn-1-ol was refluxed under $N_2$ for 4 hours. Concentration of the product on a rotovapor under a high vacuum gave 34 g of an oil. The residue was purified by high pressure liquid chromatography with 7% ethyl acetate/$CH_2Cl_2$ to yield 19.4 g of an oil which solidified on standing. 6.0 g of the alcohol was again purified by high pressure liquid chromatography with 5% ethyl acetate/$CH_2Cl_2$ to yield 5.1 g (58%) of a solid, m.p. 78°–80°.

ANALYSIS: Calculated for $C_{12}H_9Cl_2NO_3$: 50.37%C; 3.18%H; 4.89%N; Found: 50.52%C; 3.20%H; 4.71%N.

EXAMPLE 7

2-[3-(4-Chlorobenzoyl)isoxazol-5-yl]propan-1-ol

A solution of 8.7 g of 4-chlorophenylglyoxylohydroxamyl chloride in 16.7 g of 2-methyl-3-butyn-1-ol was refluxed under $N_2$ for 3 hours. The resulting mixture was concentrated under reduced pressure to give 13.5 g of an oil. This material was purified by high pressure liquid chromatography with 5% ethyl acetate/$CH_2Cl_2$ used as an eluent to give 6.3 g (59%) of an oil which solidified on standing, m.p. 49°–51°.

ANALYSIS: Calculated for $C_{13}H_{12}ClNO_3$: 58.76%C; 4.55%H; 5.27%N; Found: 59.13%C; 4.73%H; 5.15%N.

EXAMPLE 8

4-(3-Benzoylisoxazol-5-yl)butan-1-ol

A solution of 12 g of phenylglyoxylohydroxamyl chloride in 30 g of 5-hexyn-1-ol was refluxed under $N_2$ for 4 hours. Concentration of the product on a rotovapor under high vacuum gave 16 g of an oil. Purification by high pressure liquid chromatography with 5% ethyl acetate/CH$_2$Cl$_2$ used as an eluent yielded 10.0 g (62%) of an oil.

ANALYSIS: Calculated for C$_{14}$H$_{15}$NO$_3$: 68.55%C; 6.16%H; 5.71%N; Found: 68.63%C; 6.19%H; 5.52%N.

EXAMPLE 9

4-[3-(4-Chlorobenzoyl)isoxazol-5-yl]butan-1-ol

A solution of 12 g of 4-chlorophenylglyoxylohydroxamyl chloride in 30 g of 5-hexyn-1-ol was refluxed under N$_2$ for 2.5 hours. Concentration of the product on a rotovapor under high vacuum gave 18 g of an oil. Purification by high pressure liquid chromatography with 5% ethyl acetate/CH$_2$Cl$_2$ used as a eluent yielded 12.0 g (78%) of an oil which solidified on standing, m.p. 48°–51°.

ANALYSIS: Calculated for C$_{14}$H$_{14}$ClNO$_3$: 60.11%C; 5.04%H; 5.01%N; Found: 60.14%C; 5.12%H; 4.84%N.

EXAMPLE 10

4-[3-(4-Toluoyl)isoxazol-5-yl]butan-1-ol

A solution of 12 g of 4-tolylglyoxylohydroxamyl chloride in 30 g of 5-hexyn-1-ol was refluxed under N$_2$ for 3 hours. Concentration of the product on a rotovapor under high vacuum gave 20 g of an oil. Purification by high pressure liquid chromatography with 5% ethyl acetate/CH$_2$Cl$_2$ used as an eluent yielded 10.8 g (68%) of an oil.

ANALYSIS: Calculated for C$_{15}$H$_{17}$NO$_3$: 69.48%C; 6.61%H; 5.40%N; Found: 69.38%C; 6.61%H; 5.31%N.

EXAMPLE 11

4-[3-(2,4-Dichlorobenzoyl)isoxazol-5-yl]butan-1-ol

A solution of 5.0 g of 2,4-dichlorophenylglyoxylohydroxamyl chloride in 20 ml of 5-hexyn-1-ol was refluxed for 2.5 hours. The solvent was evaporated in vacuo to give 7.7 g of an oil. The residue was flash chromatographed twice with 0–4% ethyl acetate/CH$_2$Cl$_2$ to yield 4.9 g (78%) of an oil.

ANALYSIS: Calculated for C$_{14}$H$_{13}$Cl$_2$NO$_3$: 53.52%C; 4.18%H; 4.46%N; Found: 53.63%C; 4.38%H; 4.20%N.

EXAMPLE 12

(3-Benzoylisoxazol-5-yl)acetic acid

To a mixture of 8.8 g of 2-(3-benzoylisoxazol-5-yl)ethanol, in 1 liter of CH$_2$Cl$_2$, a few crystals of tetra-n-butylammonium hydrogen sulfate and 150 ml of 9M H$_2$SO$_4$ was added 11.9 g (41 mmol) of pulverized K$_2$Cr$_2$O$_7$. The resulting mixture was stirred at room temperature for 1.5 hour. After allowing the mixture to settle, it was decanted from the unreacted dichromate. The aqueous phase was extracted with CH$_2$Cl$_2$, and the organics were washed with water and brine, and dried over MgSO$_4$. Concentration gave a wet solid which was triturated with cyclohexane and collected to give 7.1 g of a solid. Recrystallization from toluene gave 4.0 g (43%) of a solid, m.p. 108°–110°.

ANALYSIS: Calculated for C$_{12}$H$_9$NO$_4$: 62.34%C; 3.92%H; 6.06%N; Found: 62.55%C; 3.95%H; 6.20%N.

EXAMPLE 13

[3-(4-Fluorobenzoyl)isoxazol-5-yl]acetic acid

To a mixture of 13.5 g of 2-[3-(4-fluorobenzoyl)-isoxazol-5-yl]ethanol and a few crystals of tetrabutylammonium hydrogen sulfate in 1 liter of CH$_2$Cl$_2$ was added 150 ml of 9M H$_2$SO$_4$. To this was added 16.9 g of pulverized K$_2$Cr$_2$O$_7$ and the mixture was stirred at room temperature for 1 hour. The organic phase was separated from the aqueous phase and washed with water. The acid product was extracted from the organic phase using 100 ml of 5% NaHCO$_3$. The alkaline solution was washed with CH$_2$Cl$_2$ several times, until all of the neutral impurities were removed, and then acidified slowly with 5% HCl. The precipitated solid was collected, washed with water and dried to yield 6.7 g of a powder. Recrystallization from 180 ml of 50% toluene/hexane gave 5.9 g (41%) of crystals, m.p. 113°–115°.

ANALYSIS: Calculated for C$_{12}$H$_8$FNO$_4$: 57.83%C; 3.24%H; 5.62%N; Found: 57.60%C; 3.34%H; 5.57%N.

EXAMPLE 14

[3-(4-Chlorobenzoyl)isoxazol-5-yl]acetic acid

To a mixture of 8.8 g of 2-[3-(4-chlorobenzoyl)isoxazol-5-yl]ethanol, 850 ml of CH$_2$Cl$_2$, a few crystals of tetra-n-butylammonium hydrogen sulfate and 130 ml of 9M H$_2$SO$_4$ was added 10.3 g of pulverized K$_2$Cr$_2$O$_7$. The resulting mixture was stirred at room temperature for 2 hours. After allowing the mixture to settle, it was decanted from the unreacted dichromate. The aqueous phase was extracted with CH$_2$Cl$_2$, and the organics were washed with water and brine, and dried over MgSO$_4$. Concentration gave 5.1 g of a solid. Recrystallization from toluene gave 3.0 g (32%) of needles, m.p. 126°–128°.

ANALYSIS: Calculated for C$_{12}$H$_8$ClNO$_4$: 54.25%C; 3.04%H; 5.27%N; Found: 54.08%C; 3.05%H; 5.23%N.

EXAMPLE 15

[3-(4-Toluoyl)isoxazol-5-yl]acetic acid

To a mixture of 10.7 g of 2-[3-(4-toluoyl)isoxazol-5-yl]ethanol, 1000 ml of CH$_2$Cl$_2$, a few crystals of tetra-n-butylammonium hydrogen sulfate and 150 ml of 9M H$_2$SO$_4$ was added 13.6 g of pulverized K$_2$Cr$_2$O$_7$. The resulting mixture was stirred at room temperature for 1.5 hour. After allowing the mixture to settle, it was decanted from the unreacted dichromate. The aqueous phase was extracted with CH$_2$Cl$_2$, and the organics were washed with water and brine, and dried over MgSO$_4$. Concentration gave 11.0 g of an oil which solidified on standing. Recrystallization from toluene gave 4.8 g (43%) of a solid, m.p. 105°–107°.

ANALYSIS: Calculated for C$_{13}$H$_{11}$NO$_4$: 63.67%C; 4.52%H; 5.71%N; Found: 63.57%C; 4.49%H; 5.69%N.

EXAMPLE 16

[3-(4-Methoxybenzoyl)isoxazol-5-yl]acetic acid

To a mixture of 24.7 g of 2-[3-(4-methoxybenzoyl)-isoxazol-5-yl]ethanol and a few crystals of tetrabutylammonium hydrogen sulfate in 2 liter of CH$_2$Cl$_2$ was added 300 ml of 9M H$_2$SO$_4$. To this was added 29.4 g of pulverized K$_2$Cr$_2$O$_7$ and the mixture was stirred at room temperature for 15 minutes. The organic phase was separated from the aqueous phase and washed with water. The acid product was extracted from the organic phase using 300 ml of 3% NaHCO$_3$. The alkaline solution was washed with CH$_2$Cl$_2$ several times, and the solution was then acidified slowly with 5% HCl until all the acid precipitated. The solid was filtered, washed with water, and dried to give 2.6 g of a powder. Recrystallization from 50 ml of toluene yielded 2.3 g (9%) of needles, m.p. 119°–121°.

ANALYSIS: Calculated for C$_{13}$H$_{11}$NO$_5$: 59.76%C; 4.25%H; 5.36%N; Found: 59.49%C; 4.21%H; 5.32%N.

EXAMPLE 17

[3-(2,4-Dichlorobenzoyl)isoxazol-5-yl]acetic acid

To a mixture of 12.8 g of 2-[3-(2,4-dichlorobenzoyl)-isoxazol-5-yl]ethanol and a few crystals of tetra-n-butylammonium hydrogen sulfate in 1000 ml of $CH_2Cl_2$ was added 150 ml of 9M $H_2SO_4$. To this was added 13.2 g of pulverized $K_2Cr_2O_7$ and the mixture was stirred at room temperature for 1 hour. The organic phase was separated from the aqueous phase and washed with water. The acid product was extracted from the organic phase using 40 ml of 4% $NaHCO_3$. The alkaline solution was washed with $CH_2Cl_2$ several times, until all the neutral impurities were removed, and the solution was then acidified slowly with 5% HCl until all the acid precipitated. The solid was filtered, washed with water, and dried to yield 3.9 g of a powder. Recrystallization from 100 ml of 50% toluene/hexane gave 3.5 g (26%) of crystals, m.p. 108°–109°.

ANALYSIS: Calculated for $C_{12}H_7Cl_2NO_4$: 48.03%C; 2.36%H; 4.67%N; Found: 47.83%C; 2.44%H; 4.59%N.

EXAMPLE 18

2-[3-(4-Chlorobenzoyl)isoxazol-5-yl]propionic acid

To a mixture of 11.0 g of 2-[3-(4-chlorobenzoyl)-isoxazol-5-yl]propan-1-ol in 1000 ml of $CH_2Cl_2$, a few crystals of tetra-n-butylammonium hydrogen sulfate and 150 ml of 9M $H_2SO_4$ was added 12.3 g of pulverized $K_2Cr_2O_7$. The resulting mixture was stirred at room temperature for 1.5 hour. After allowing the mixture to settle, it was decanted from the unreacted dichromate. The aqueous phase was separated and the organics were washed with water and brine, and dried over $MgSO_4$. Concentration of the product gave 8.0 g of a solid. Recrystallization from toluene with norite for decolorizing gave 2.0 g of a solid, m.p. 119°–123°. A second recrystallization from toluene gave 1.6 g (13%) of a solid, m.p. 122.5°–124.5°.

ANALYSIS: Calculated for $C_{13}H_{10}ClNO_4$: 55.83%C; 3.60%H; 5.01%N; Found: 55.46%C; 3.51%H; 4.95%N.

EXAMPLE 19

4-Chlorophenyl-[(5-phenylthiomethyl)isoxazol-3-yl]methanone

A mixture of 32.7 g of 4-chlorophenylglyoxylohydroxamyl chloride and 89.3 g of 80% propargyl bromide in toluene was refluxed under $N_2$ overnight. The volatiles were removed by short-path distillation and the residue was recrystallized from EtOH to give 28 g of a crystalline solid, m.p. 85°–87.5°. This bromomethyl compound was used as such in the next step.

A solution of 12 ml of $Et_3N$ in 35 ml of $Et_2O$ was added dropwise to a solution consisting of 13 g of the bromo compound above, 4.4 ml of thiophenol and 120 ml of 20% acetone/$Et_2O$. The reaction mixture was stirred at room temperature for 1 hour and allowed to stand at room temperature overnight. After dilution with $Et_2O$, the organics were washed with water, 5% aqueous HCl, saturated $NaHCO_3$ and saturated NaCl, and dried over $MgSO_4$. The solution was concentrated to give an oil. Purification by high pressure liquid chromatography using 50% $CH_2Cl_2$/hexane yielded 10.9 g (48%) of an oil which solidified on standing, m.p. 54°–56°.

ANALYSIS: Calculated for $C_{17}H_{12}ClNO_2S$: 61.91%C; 3.67%H; 4.25%N; Found: 61.52%C; 3.55%H; 4.20%N.

EXAMPLE 20

4-Chlorophenyl-[(5-phenylsulfinylmethyl)isoxazol-3-yl]methanone

A solution of 4.45 g of m-chloroperoxybenzoic acid, (85% purity) in 100 ml of $CH_2Cl_2$ was added dropwise under $N_2$ to a solution of 6.0 g of 4-chlorophenyl-[(5-phenylthiomethyl)isoxazol-3-yl]-methanone in 150 ml of $CH_2Cl_2$ at −70°. After 30 minutes at −70°, the reaction mixture was poured directly into a mixture of 200 ml of 10% aqueous $Na_2S_2O_3$ and 400 ml of $Et_2O$. The organics were washed with saturated $NaHCO_3$ and dried over $MgSO_4$. Concentration of the product gave 5.8 g of a solid which was recrystallized from acetone/hexane to yield 3.4 g (55%) of a solid, m.p. 118°–120°.

ANALYSIS: Calculated for $C_{17}H_{12}ClNO_3S$: 59.04%C; 3.50%H; 4.05%N; Found: 59.39%C; 3.54%H; 4.26%N.

EXAMPLE 21

(5-Dimethylaminomethylisoxazol-3-yl)-4-fluorophenylmethanone maleate

A 50% $Et_2O$/MeOH mixture (250 ml) was saturated with dimethylamine gas and cooled in an ice-bath. To this was added a solution of 4.5 g of (5-bromomethylisoxazol-3-yl)-4-fluorophenylmethanone in 25 ml of $Et_2O$. The resulting solution was allowed to warm to room temperature and stirred for two days. The methanol was evaporated in vacuo to give an residue, which was dissolved in 500 ml of EtOAc. The solution was washed with water until neutral and with saturated NaCl, dried over $Na_2SO_4$, and evaporated to give 3.5 g of an oil which solidified on standing.

A solution of 2.8 g of the amine in 30 ml of $CH_2Cl_2$ was filtered and added dropwise to a solution of 1.74 g maleic acid in 400 ml of $Et_2O$. The precipitated salt was filtered and recrystallized from 60 ml of 2-propanol to yield 3.45 g (74%) of crystals, m.p. 134°–135°.

ANALYSIS: Calculated for $C_{13}H_{13}FN_2O_2 \cdot C_4H_4O_4$: 56.04%C; 4.71%H; 7.69%N; Found: 56.18%C; 4.76%H; 7.68%N.

EXAMPLE 22

(5-(Morpholin-4-yl)methylisoxazol-3-yl]-4-fluorophenylmethanone

A solution of 4.5 g of (5-bromomethylisoxazol-3-yl-4-fluorophenylmethanone in 100 ml of $Et_2O$ was added dropwise to a solution of 7 ml of morpholine in 300 ml of 50% acetone/$Et_2O$. The resulting mixture was stirred at room temperature for 20 hours. This mixture was filtered and the volatiles evaporated to give a residue which was dissolved in 600 ml of $Et_2O$. The organic solution was washed with water until it became neutral and then with saturated NaCl, and dried over $Na_2SO_4$ and concentrated in vacuo to give 4.3 g of a crystalline solid. A 3.6 g sample of the amine was recrystallized from 65 ml of 8% toluene/hexane to yield 2.4 g (64%) of crystals, m.p. 72°–74°.

ANALYSIS: Calculated for $C_{15}H_{15}FN_2O_3$: 62.06%C; 5.22%H; 9.65%N; Found: 61.79%C; 5.15%H; 9.64%N.

EXAMPLE 23

[5-(Morpholin-4-yl)methylisoxazol-3-yl]-4-chlorophenylmethanone maleate 7.0 ml of morpholine was added to a solution of 6.0 g of (5-bromomethylisoxazol-3-yl)-4-chlorophenylmethanone in 100 ml of 50% acetone/Et$_2$O. The resulting solution was stirred at room temperature for 2 days. This mixture was filtered and the volatiles evaporated to give a residue which was dissolved in 400 ml of Et$_2$O. The organic solution was washed with water until neutral and with saturated NaCl, dried over Na$_2$SO$_4$ and concentrated in vacuo to give an oil. The residue was flash chromatographed with 40% hexane/ethyl acetate to give 6.1 g of an oil which solidified.

A solution of the amine in 50 ml of Et$_2$O was added dropwise to a solution of 2.6 g of maleic acid in 500 ml of Et$_2$O. The precipitated salt was filtered and recrystallized from 150 ml of EtOH to yield 5.8 g (69%) of crystals, m.p. 148°–149°.

ANALYSIS: Calculated for C$_{15}$H$_{15}$ClN$_2$O$_3$!C$_4$H$_4$O$_4$: 53.97%C; 4.54%H; 6.62%N; Found: 53.89%C; 4.59%H; 6.69%N.

EXAMPLE 24

[5-(4-beta-Hydroxyethylpiperazin-1-yl)methylisoxazol-3-yl]-4-fluorophenylmethanone dimaleate A solution of 5.7 g of (5-bromomethylisoxazol-3-yl)-4-fluorophenylmethanone in 100 ml of Et$_2$O was added to a solution of 6.5 g of N-beta-hydroxyethylpiperazine in 400 ml of 25% acetone/Et$_2$O. The resulting mixture was stirred at room temperature for 24 hours. This mixture was filtered and the solution was concentrated in vacuo to give an oil. The residue was dissolved in 300 ml of H$_2$O and shortly thereafter a precipitate formed. The solid was filtered and dried to give 5.2 g of crude solid. A solution of 4.3 g of the amine in 50 ml of 50% ethyl acetate/CH$_2$Cl$_2$ was added dropwise to a solution of excess maleic acid in 600 ml of Et$_2$O. The precipitated salt was filtered and recrystallized from 160 ml of isopropanol to yield 5.2 g (55%) of crystals, m.p. 139°–140°.

ANALYSIS: Calculated for C$_{17}$H$_{20}$FN$_2$O$_3$!2(C$_4$H$_4$O$_4$): 53.09%C; 5.00%H; 7.43%N; Found: 53.29%C; 5.01%H; 7.56%N.

EXAMPLE 25

[5-[(4-Phenylpiperazin-1-yl)methyl]isoxazol-3-yl]phenylmethanone

A solution of 3.5 g of (5-bromomethylisoxazol-3-yl)-phenylmethanone in 100 ml of Et$_2$O was added dropwise to a solution of 8.6 g of phenylpiperazine in 375 ml of 20% acetone/Et$_2$O. The resulting mixture was stirred at room temperature for 72 hours. This mixture was washed with water and brine, and dried over MgSO$_4$. Concentration of the product gave an oil, which was taken up in 500 ml of CH$_2$Cl$_2$ and stirred with 20 g of silica gel overnight. The silica was removed by filtration and washed with 500 ml of CH$_2$Cl$_2$. The combined filtrates were concentrated to give 4.7 g of an oil which solidified on standing. Recrystallization from ethanol yielded 3.1 g (69%) of platelets, m.p. 100°–102° C.

ANALYSIS: Calculated for C$_{21}$H$_{21}$N$_3$O$_2$: 72.60%C; 6.09%H; 12.10%N; Found: 72.90%C; 6.18%H; 11.95%N.

EXAMPLE 26

[5-(4-Phenylpiperazin-1-yl)methylisoxazol-3-yl]-4-fluorophenylmethanone

A solution of 3.7 g of (5-bromomethylisoxazol-3-yl)-4-fluorophenylmethanone in 100 ml of Et$_2$O was added dropwise to a solution of 5.2 g of N-phenylpiperazine in 400 ml of 20% acetone/Et$_2$O. The resulting mixture was stirred at room temperature for 24 hours. This mixture was filtered and the solution was washed with water (2×200 ml) and saturated NaCl, and dried over MgSO$_4$. Concentration of the product gave 5.5 g of a solid which was dissolved in 100 ml of CH$_2$Cl$_2$ and stirred with 5 g of SiO$_2$. This mixture was filtered, the silica washed with CH$_2$Cl$_2$, and the organics were evaporated to give 3.7 g of a solid. The amine was recrystallized from 135 ml of 8% toluene/hexane to yield 2.5 g (53%) of needles, m.p. 94°–95°.

ANALYSIS: Calculated for C$_{21}$H$_{20}$FN$_3$O$_2$: 69.02%C; 5.53%H; 11.49%N; Found: 69.16%C; 5.66%H; 11.50%N.

EXAMPLE 27

[5-[4-(2,3,4-Trimethoxybenzyl)piperazin-1-yl]methylisoxazol-3-yl]-4-fluorophenylmethanone dimaleate A solution of 3.1 g of (5-bromomethylisoxazol-3-yl)-4-fluorophenylmethanone in 50 ml of tetrahydrofuran was added to a solution consisting of 3.5 g of N-2,3,4-trimethoxybenzylpiperazine, 1.8 ml of triethylamine and 50 ml of CH$_3$OH. After stirring at room temperature overnight, the mixture was concentrated to a residue. This material was flash chromatographed, using ethyl acetate as an eluent, to give 3.8 g of a solid. A solution of this compound in 30 ml of CH$_2$Cl$_2$ was added to a solution of 2.6 g of maleic acid in 500 ml of Et$_2$O. The collected solid was recrystallized from acetonitrile to give 4.4 g (57%) of a solid, m.p. 154°–155°.

ANALYSIS: Calculated for C$_{25}$H$_{28}$FN$_3$O$_5$!2C$_4$H$_4$O$_4$: 56.49%C; 5.17%H; 5.99%N; Found: 56.40%C; 5.18%H; 5.92%N.

EXAMPLE 28

[5-[4-(2,3,4-Trimethoxybenzyl)piperazin-1-yl]methylisoxazol-3-yl]-4-methoxyphenylmethanone dimaleate A solution of 3.3 g of (5-bromomethylisoxazol-3-yl)-4-methoxyphenylmethanone in 50 ml of tetrahydrofuran was added to a solution consisting of 3.5 g of N-2,3,4-trimethoxybenzylpiperazine, 1.8 ml of triethylamine and 50 ml of CH$_3$OH. After stirring at room temperature overnight, the mixture was concentrated to a residue. This material was flash chromatographed, using ethyl acetate as an eluent, to give 4.0 g of an oil. A solution of this compound in 30 ml of CH$_2$Cl$_2$ was added to a solution of 2.6 g of maleic acid in 500 ml of Et$_2$O. The collected solid was recrystallized from acetonitrile to give 3.6 g (46%) of a solid, m.p. 147°–149°.

ANALYSIS: Calculated for C$_{26}$H$_{31}$N$_3$O$_6$!2C$_4$H$_4$O$_4$: 57.22%C; 5.51%H; 5.89%N; Found: 57.21%C; 5.51%H; 5.89%N.

EXAMPLE 29

[5-(4-Benzhydrylpiperazin-1-yl)methylisoxazol-3-yl]-phenylmethanone dimaleate

A solution of 5.0 g of N-benzhydrylpiperazine in 100 ml of MeOH was added to a solution of 4.0 g of (5-bromomethylisoxazol-3-yl)-phenylmethanone in 40 ml of Et$_2$O. To this was added 2.8 ml of triethylamine and the resultant solution stirred for 20 hours. The volatiles were evaporated to give a solid residue which was dissolved in 100 ml of CH$_2$Cl$_2$. The organic solution was washed with 5% Na$_2$CO$_3$, water and saturated NaCl, dried over Na$_2$SO$_4$ and concentrated in vacuo to give 8.4 g of an oil. The residue was flash chromatographed with 0–4% ethyl acetate/$CH_2Cl_2$ to yield 6.2 g of amine.

A solution of the amine in 25 ml of $CH_2Cl_2$ was added to a solution of 3.6 g of maleic acid in 700 ml of $Et_2O$. The precipitated salt was filtered and recrystallized from 600 ml of isopropanol to yield 7.1 g (71%) of crystals, m.p. 174°–176°.

ANALYSIS: Calculated for $C_{28}H_{27}N_3O_2!2(C_4H_4O_4)$: 64.56%C; 5.28%H; 6.27%N; Found: 64.45%C; 5.28%H; 6.10%N.

EXAMPLE 30

[5-(4-Benzhydrylpiperazin-1-yl)methylisoxazol-3-yl]-4-fluorophenylmethanone dimaleate A solution of 2.8 g of (5-bromomethylisoxazol-3-yl)-4-fluorophenylmethanone in 100 ml of tetrahydrofuran was added to a solution consisting of 3.0 g of N-benzhydrylpiperazine, 1.7 ml of triethylamine and 50 ml of MeOH. The resultant solution was stirred at room temperature for 3 days. The volatiles were evaporated to give a residue which was flash chromatographed with 25% ethyl acetate/hexane to give 3.4 g of an oil which solidified.

A solution of the amine in 40 ml of $CH_2Cl_2$ was added to a solution of 2.0 g maleic acid in 700 ml of $Et_2O$. The precipitated salt was filtered and recrystallized from 300 ml of acetonitrile to yield 4.8 g (70%) of crystals, m.p. 180°–181°.

ANALYSIS: Calculated for $C_{28}H_{26}FN_3O_2!2(C_4H_4O_4)$: 62.87%C; 4.99%H; 6.11%N; Found: 62.76%C; 4.89%H; 6.08%N.

EXAMPLE 31

[5-(4-Benzhydrylpiperazin-1-yl)methylisoxazol-3-yl]-4-chlorophenylmethanone dimaleate A solution of 4.0 g of N-benzhydrylpiperazine in 100 ml of MeOH was added to a solution of 3.9 g of (5-bromomethylisoxazol-3-yl)-4-chlorophenylmethanone in 30 ml of tetrahydrofuran. To this was added 2.2 ml of triethylamine and the solution stirred for 20 hours. The volatiles were evaporated to give a residue which was dissolved in 350 ml of ethyl acetate. The solution was washed with 5% $Na_2CO_3$, water and saturated NaCl, dried over $Na_2SO_4$ and concentrated in vacuo to give a solid. The residue was flash chromatogrphed with 25% ethyl acetate/hexane to yield 5.8 g of the amine, m.p. 137°–139°.

A solution of the amine in 40 ml of $CH_2Cl_2$ was added to a solution of 3.1 g of maleic acid in 600 ml of $Et_2O$. The precipitated salt was filtered and recrystallized from 700 ml of acetonitrile to yield 7.4 g (81%) of crystals, m.p. 185°–186°.

ANALYSIS: Calculated for $C_{28}H_{26}ClN_3O_2!2(C_4H_4O_4)$: 61.40%C; 4.88%H; 5.96%N; Found: 61.45%C; 4.96%H; 6.03%N.

EXAMPLE 32

[5-(4-Benzhydrylpiperazin-1-yl)methylisoxazol-3-yl]-4-methoxyphenylmethanone dimaleate A solution of 2.95 g of (5-bromomethylisoxazol-3-yl)-4-methoxyphenylmethanone in 30 ml of tetrahydrofuran was added to a solution consisting of 3.0 g of N-benzhydrylpiperazine, 1.7 ml of triethylamine and 70 ml of MeOH. The resultant solution was stirred at room temperature for 3 days. The volatiles were evaporated to give a residue which was flash chromatographed with 25% ethyl acetate/hexane to give 4.1 g of an oil.

A solution of the amine in 30 ml of $CH_2Cl_2$ was added to a solution of 2.3 g of maleic acid in 500 ml of $Et_2O$. The precipitated salt was filtered and recrystallized from 400 ml of acetonitrile to yield 5.2 g (74%) of crystals, m.p. 174°–176°.

ANALYSIS: Calculated for $C_{29}H_{29}N_3O_3!2(C_4H_4O_4)$: 63.51%C; 5.34%H; 6.00%N; Found: 63.48%C; 5.33%H; 6.17%N.

EXAMPLE 33

[5-[4-(4,4'-Difluorobenzhydryl)piperazin-1-yl]methylisoxazol-3-yl]phenylmethanone dimaleate A solution of 4.25 g of (5-bromomethylisoxazol-3-yl)-phenylmethanone in 40 ml of $Et_2O$ was added to a solution consisting of 5.8 g of N-4,4'-difluorobenzhydrylpiperazine, 2.8 ml of triethylamine and 100 ml of MeOH. The resultant solution was stirred at room temperature for 16 hours. The volatiles were evaporated to give a residue which was dissolved in 150 ml of ethyl acetate. The solution was washed with diluted $Na_2CO_3$, water and saturated NaCl, dried over $Na_2SO_4$ and concentrated in vacuo to give an oil. The residue was flash chromatographed with 25% ethyl acetate/hexane to give 7.6 g of an oil. A solution of the amine in 40 ml of $Et_2O$ was added to a solution of 4.1 g of maleic acid in 700 ml of $Et_2O$. The precipitated salt was filtered and recrystallized from 300 ml of acetonitrile to yield 6.5 g (58%) of crystals, m.p. 175°–177°.

ANALYSIS: Calculated for $C_{28}H_{25}F_2N_3O_2!2(C_4H_4O_4)$: 61.27%C; 4.72%H; 5.95%N; Found: 61.17%C; 4.63%H; 6.01%N.

EXAMPLE 34

[5-[4-(4,4'-Difluorobenzhydryl)piperazin-1-yl]methylisoxazol-3-yl]-4-fluorophenylmethanone dimaleate A solution of 2.8 g of (5-bromomethylisoxazol-3-yl)-4-fluorophenylmethanone in 65 ml of tetrahydrofuran was added to a solution consisting of 3.5 g of N-4,4'-difluorobenzhydrylpiperazine, 1.7 ml of triethylamine and 50 ml of MeOH. The resultant solution was stirred at room temperature for 16 hours. The volatiles were evaporated to give a residue which as flash chromatographed with 25% ethyl acetate/hexane to give 4.6 g of a resin.

A solution of the amine in 40 ml of $CH_2Cl_2$ was added to a solution of 2.6 g of maleic acid in 800 ml of $Et_2O$. The precipitated salt was filtered and recrystallized from 400 ml of acetonitrile to yield 4.5 g (62%) of crystals, m.p. 184°–186°.

ANALYSIS: Calculated for $C_{28}H_{24}F_3N_3O_2!2(C_4H_4O_4)$: 59.74%C; 4.47%H; 5.80%N; Found: 59.82%C; 4.51%H; 5.95%N.

EXAMPLE 35

[5-[4-(4,4'-Difluorobenzhydryl)piperazin-1-yl]methylisoxazol-3-yl]-4-chlorophenylmethanone dimaleate A solution of 3.9 ml of (5-bromomethylisoxazol-3-yl)-4-chlorophenylmethanone in 30 ml of tetrahydrofuran was added to a solution consisting of 4.6 g of N-4,4'-difluorobenzhydrylpiperazine, 2.2 ml of triethylamine and 100 ml of MeOH. The resultant solution was stirred at room temperature for 16 hours. The volatiles were evaporated to give a residue which was dissolved in 150 ml of ethyl acetate. The solution was washed with diluted $Na_2CO_3$, water and saturated NaCl, dried over $Na_2SO_4$, and concentrated in vacuo to give 9.4 g of an oil. The residue was flash chromatographed with 25% ethyl acetate/hexane to give 7.1 g of an oil.

A solution of the amine in 40 ml of $CH_2Cl_2$ was added to a solution of 3.2 g of maleic acid in 900 ml of $Et_2O$. The flocculent salt was filtered and recrystallized from 600 ml of acetonitrile to yield 7.1 g (74%) of crystals, m.p. 183°–184°.

ANALYSIS: Calculated for $C_{28}H_{24}ClF_2N_3O_2!2(C_4H_4O_4)$: 58.42%C; 4.37%H; 5.67%N; Found: 58.48%C; 4.44%H; 5.70%N.

EXAMPLE 36

[5-[4-(4,4′-Difluorobenzhydryl)piperazin-1-yl]methylisoxazol-3-yl]-4-methoxyphenlymethanone dimaleate A solution of 2.95 g of (5-bromomethylisoxazol-3-yl)-4-methoxyphenylmethanone in 20 ml of tetrahydrofuran was added to a solution consisting of 3.5 g of N-4,4′-difluorobenzhydrylpiperazine, 1.7 ml of triethylamine and 50 ml of MeOH. The resultant solution was stirred at room temperature for 3 days. The volatiles were evaporated to give a residue which was flash chromatographed with 25% ethyl acetate/hexane to give 3.7 g of an oil.

A solution of the amine in 20 ml of $CH_2Cl_2$ was added to a solution of 2.3 g of maleic acid in 600 ml of $Et_2O$. The precipitated salt was filtered and recrystallized from 220 ml of acetonitrile to yield 4.5 g (61%) of crystals, m.p. 175°–176°.

ANALYSIS: Calculated for $C_{29}H_{27}F_2N_3O_3!2(C_4H_4O_4)$: 60.40%C; 4.80%H; 5.71%N; Found: 60.70%C; 4.77%H; 5.87%N.

We claim:

1. A compound having the formula

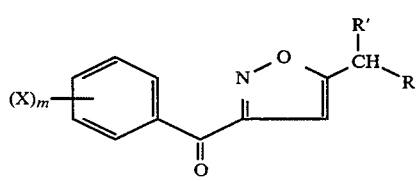

where each X is independently hydrogen, halogen, loweralkyl or loweralkoxy; m is 1 or 2; R′ is hydrogen or loweralkyl; and R is

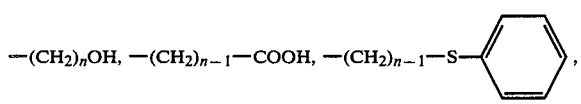

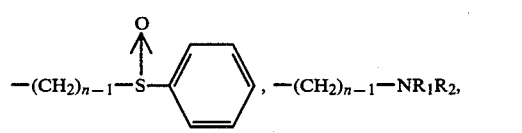

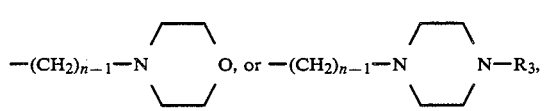

n being 1, 2 or 3, each of $R_1$ and $R_2$ being independently hydrogen or loweralkyl and $R_3$ being —$(CH_2)_2OH$,

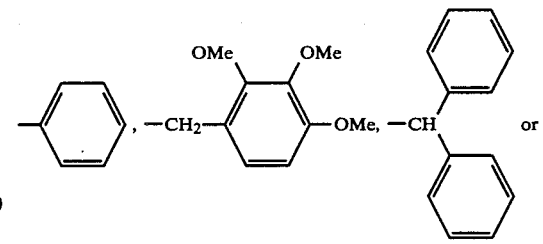

an optical antipode thereof, or a pharmaceutically acceptable acid addition salt thereof.

2. The compound as defined in claim 1, where R is —$CH_2OH$.

3. The compound as defined in claim 2, where R′ is hydrogen and m is 1.

4. The compound as defined in claim 3, where X is hydrogen, which is 2-(3-benzoylisoxazole-5-yl)ethanol.

5. The compound as defined in claim 3, where X is halogen.

6. The compound as defined in claim 5, where X is fluorine.

7. The compound as defined in claim 6, where X is 4-fluoro, which is 2-[3-(4-fluorobenzoyl)isoxazol-5-yl]ethanol.

8. The compound as defined in claim 5, where X is chlorine.

9. The compound as defined in claim 8, where X is 4-chloro, which is 2-[3-(4-chlorobenzoyl)isoxazol-5-yl]ethanol.

10. The compound as defined in claim 3, where X is loweralkyl.

11. The compound as defined in claim 10, where X is methyl.

12. The compound as defined in claim 11, where X is 4-methyl, which is 2-[3-(4-toluoyl)isoxazol-5-yl]ethanol.

13. The compound as defined in claim 3, where X is methoxy.

14. The compound as defined in claim 13, where X is 4-methoxy, which is 2-[3-(4-methoxybenzoyl)isoxazol-5-yl]ethanol.

15. The compound as defined in claim 2, where R′ is hydrogen and m is 2.

16. The compound as defined in claim 15, where $(X)_m$ is dichloro.

17. The compound as defined in claim 16, where $(X)_m$ is 2,4-dichloro, which is 2-[3-(2,4-dichlorobenzoyl)isoxazol-5-yl]ethanol.

18. The compound as defined in claim 2, where R′ is methyl and m is 1.

19. The compound as defined in claim 18, where X is halogen.

20. The compound as defined in claim 19, where X is chlorine.

21. The compound as defined in claim 20, where X is 4-chloro, which is 2-[3-(4-chlorobenzoyl)isoxazol-5-yl]propan-1-ol.

22. The compound as defined in claim 1, where R is —(CH₂)₃OH.

23. The compound as defined in claim 22, where R' is hydrogen and m is 1.

24. The compound as defined in claim 23, where X is hydrogen, which is 4-(3-benzoylisoxazol-5-yl)butan-1-ol.

25. The compound as defined in claim 23, where X is halogen.

26. The compound as defined in claim 25, where X is chlorine.

27. The compound as defined in claim 26, where X is 4-chloro, which is 4-[3-(4-chlorobenzoyl)isoxazol-5-yl]butan-1-ol.

28. The compound as defined in claim 23, where X is loweralkyl.

29. The compound as defined in claim 28, where X is methyl.

30. The compound as defined in claim 29, where X is 4-methyl, which is 4-[3-(4-toluoyl)isoxazol-5-yl]butan-1-ol.

31. The compound as defined in claim 22, where R' is hydrogen and m is 2.

32. The compound as defined in claim 31, where (X)$_m$ is dichloro.

33. The compound as defined in claim 32, where (X)$_m$ is 2,4-dichloro, which is 4-[3-(2,4-dichlorobenzoyl)isoxazol-5-yl]butan-1-ol.

34. The compound as defined in claim 1, where R is —COOH.

35. The compound as defined in claim 34, where R' is hydrogen and m is 1.

36. The compound as defined in claim 35, where X is hydrogen, which is (3-benzoylisoxazol-5-yl)acetic acid.

37. The compound as defined in claim 35, where X is halogen.

38. The compound as defined in claim 37, where X is fluorine.

39. The compound as defined in claim 38, where X is 4-fluoro, which is [3-(4-fluorobenzoyl)isoxazol-5-yl]acetic acid.

40. The compound as defined in claim 37, where X is chlorine.

41. The compound as defined in claim 40, where X is 4-chloro, which is [3-(4-chlorobenzoyl)isoxazol-5-yl]acetic acid.

42. The compound as defined in claim 35, where X is loweralkyl.

43. The compound as defined in claim 42, where X is methyl.

44. The compound as defined in claim 43, where X is 4-methyl, which is [3-(4-toluoyl)isoxazol-5-yl]acetic acid.

45. The compound as defined in claim 35, where X is methoxy.

46. The compound as defined in claim 45, where X is 4-methoxy, which is [3-(4-Methoxybenzoyl)isoxazol-5-yl]acetic acid.

47. The compound as defined in claim 34, where R' is hydrogen and m is 2.

48. The compound as defined in claim 47, where (X)$_m$ is dichloro.

49. The compound as defined in claim 48, where (X)$_m$ is 2,4-dichloro, which is [3-(2,4-dichlorobenzoyl)isoxazol-5-yl]acetic acid.

50. The compound as defined in claim 34, where R' is methyl and m is 1.

51. The compound as defined in claim 50, where X is halogen.

52. The compound as defined in claim 51, where X is chlorine.

53. The compound as defined in claim 52, where X is 4-chloro, which is 2-[3-(4-chlorobenzoyl)isoxazol-5-yl]propionic acid.

54. The compound as defined in claim 1, where R is

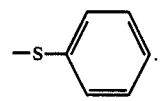

55. The compound as defined in claim 54, where R' is hydrogen and m is 1.

56. The compound as defined in claim 55, where X is halogen.

57. The compound as defined in claim 56, where X is chlorine.

58. The compound as defined in claim 57, where X is 4-chloro, which is 4-chlorophenyl-[(5-phenylthiomethyl)isoxazol-3-yl]methanone.

59. The compound as defined in claim 1, where R is

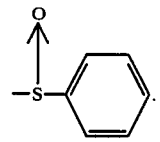

60. The compound as defined in claim 59, where R' is hydrogen and m is 1.

61. The compound as defined in claim 60, where X is halogen.

62. The compound as defined in claim 61, where X is chlorine.

63. The compound as defined in claim 62, where X is 4-chloro, which is 4-chlorophenyl-[(5-phenylsulfinylmethyl)isoxazol-3-yl]-methanone.

64. The compound as defined in claim 1, where R is —NR₁R₂.

65. The compound as defined in claim 64, where R₁ is loweralkyl and R₂ is loweralkyl.

66. The compound as defined in claim 65, where R₁ is methyl and R₂ is methyl.

67. The compound as defined in claim 66, where R' is hydrogen and m is 1.

68. The compound as defined in claim 67, where X is halogen.

69. The compound as defined in claim 68, where X is fluorine.

70. The compound as defined in claim 69, where X is 4-fluoro, which is (5-dimethylaminomethylisoxazol-3-yl)-4-fluorophenylmethanone maleate.

71. The compound as defined in claim 1, where R is

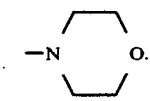

72. The compound as defined in claim 71, where R' is hydrogen and m is 1.
73. The compound as defined in claim 72, where X is halogen.
74. The compound as defined in claim 73, where X if fluorine.
75. The compound as defined in claim 74, where X is 4-fluoro, which is (5-(morpholin-4-yl)methylisoxazol-3-yl]-4-fluorophenylmethanone.
76. The compound as defined in claim 73, where X is chlorine.
77. The compound as defined in claim 76, where X is 4-chloro, which is [5-(morpholin-4-yl)methylisoxazol-3-yl]-4-chlorophenylmethanone maleate.
78. The compound as defined in claim 1, where R is

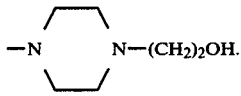

79. The compound as defined in claim 78, where R' is hydrogen and m is 1.
80. The compound as defined in claim 79, where X is halogen.
81. The compound as defined in claim 80, where X is fluorine.
82. The compound as defined in claim 81, where X is 4-fluoro, which is [5-(4-beta-hydroxyethylpiperazin-1-yl)methylisoxazol-3-yl]-4-fluorophenylmethanone dimaleate.
83. The compound as defined in claim 1, where R is

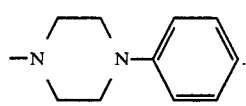

84. The compound as defined in claim 83, where R' is hydrogen and m is 1.
85. The compound as defined in claim 84, where X is hydrogen, which is [5-[(4-phenylpiperazin-1-yl)methyl]isoxazol-3-yl]-phenylmethanone.
86. The compound as defined in claim 84, where X is halogen.
87. The compound as defined in claim 86, where X is 4-fluoro, which is [5-(4-phenylpiperazin-1-yl)methylisoxazol-3-yl]-4-fluorophenylmethanone.
88. The compound as defined in claim 1, where R is

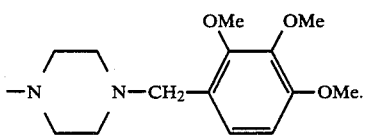

89. The compound as defined in claim 88, where R' is hydrogen and m is 1.
90. The compound as defined in claim 89, where X is halogen.
91. The compound as defined in claim 90, where X is fluorine.
92. The compound as defined in claim 91, where X is 4-fluoro, which is [5-[4-(2,3,4-trimethoxybenzyl)piperazin-1-yl]methylisoxazol-3-yl]-4-fluorophenylmethanone dimaleate.
93. The compound as defined in claim 89, where X is methoxy.
94. The compound as defined in claim 93, where X is 4-methoxy, which is [5-[4-(2,3,4-trimethoxybenzyl)piperazin-1-yl]methylisoxazol-3-yl]-4-methoxyphenylmethanone dimaleate.
95. The compound as defined in claim 1, R is

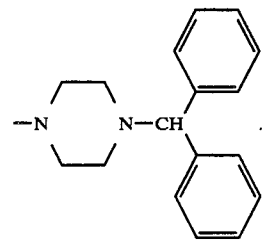

96. The compound as defined in claim 95, where R' is hydrogen and m is 1.
97. The compound as defined in claim 96, where X is hydrogen, which is [5-(4-benzhydrylpiperazin-1-yl)methylisoxazol-3-yl]-phenylmethanone dimaleate.
98. The compound as defined in claim 97, where X is halogen.
99. The compound as defined in claim 98, where X is fluorine.
100. The compound as defined in claim 99, where X is 4-fluoro, which is [5-(4-benzhydrylpiperazin-1-yl)methylisoxazol-3-yl]-4-fluorophenylmethanone dimaleate.
101. The compound as defined in claim 98, where X is chlorine.
102. The compound as defined in claim 101, where X is 4-chloro, which is [5-(4-benzhydrylpiperazin-1-yl)methylisoxazol-3-yl]-4-chlorophenylmethanone dimaleate.
103. The compound as defined in claim 96, where X is methoxy.
104. The compound as defined in claim 103, where X is 4-methoxy, which is [5-(4-benzhydrylpiperazin-1-yl)methylisoxazol-3-yl]-4-methoxyphenylmethanone dimaleate.
105. The compound as defined in claim 1, where R is

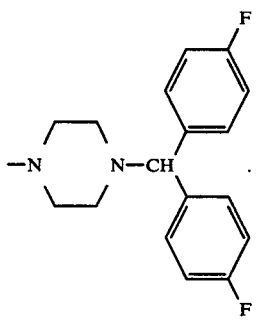

106. The compound as defined in claim 105, where R' is hydrogen and m is 1.

107. The compound as defined in claim 106, where X is hydrogen, which is [5-[4-(4,4'-difluorobenzhydryl)-piperazin-1-yl]methylisoxazol-3-yl]phenylmethanone.

108. The compound as defined in claim 106, where X is halogen.

109. The compound as defined in claim 108, where X is fluorine.

110. The compound as defined in claim 109, where X is 4-fluoro, which is [5-[4-(4,4'-difluorobenzhydryl)-piperazin-1-yl]methylisoxazol-3-yl]-4-fluorophenyl-methanone.

111. The compound as defined in claim 108, where X is chlorine.

112. The compound as defined in claim 111, where X is 4-chloro, which is [5-[4-(4,4'-difluorobenzhydryl)-piperazin-1-yl]methylisoxazol-3-yl]-4-chlorophenyl-methanone.

113. The compound as defined in claim 106, where X is methoxy.

114. The compound as defined in claim 113, where X is 4-methoxy, which is [5-[4-(4,4'-difluorobenzhydryl)-piperazin-1-yl]methylisoxazol-3-yl]-4-methoxyphenyl-methanone.

115. A pharmaceutical composition comprising an effective amount of a compound defined in claim 1 in association with a carrier or diluent.

116. A method of treating a patient in need of depressing blood pressure which comprises administering to the patient an effective blood pressure depressing amount of a compound defined in claim 1.

117. A method of treating a patient in need of alleviating pain which comprises administering to the patient an effective pain alleviating amount of a compound defined in claim 1.

118. A method of treating a patient in need of suppressing inflammation which comprises administering to the patient an effective inflammation suppressing amount of a compound defined in claim 1.

* * * * *